United States Patent
Hartley

(10) Patent No.: US 6,860,463 B2
(45) Date of Patent: Mar. 1, 2005

(54) ACCESS VALVE

(75) Inventor: David Ernest Hartley, Western Australia (AU)

(73) Assignees: William A. Cook Australia Pty. Ltd., Queensland (AU); Cook Incorporated, Bloomington, IN (US)

(*) Notice: Subject to any disclaimer, the term of this patent is extended or adjusted under 35 U.S.C. 154(b) by 203 days.

(21) Appl. No.: 10/309,485

(22) Filed: Dec. 4, 2002

(65) Prior Publication Data

US 2003/0116731 A1 Jun. 26, 2003

(30) Foreign Application Priority Data

Dec. 4, 2001 (AU) .............................. PR 9290

(51) Int. Cl.[7] ................................................ F16K 7/04
(52) U.S. Cl. ........................ 251/4; 251/294; 251/297; 604/34
(58) Field of Search .............................. 251/4, 7, 294, 251/297; 604/30, 34

(56) References Cited

U.S. PATENT DOCUMENTS

| | | |
|---|---|---|
| 2,846,179 A | 8/1958 | Monckton |
| 4,092,010 A | 5/1978 | Carlson, Jr. |
| 4,195,810 A | 4/1980 | Lavin |
| 4,412,669 A | 11/1983 | Hanyu et al. |
| 4,821,996 A * | 4/1989 | Bellotti et al. ............... 251/4 |
| 4,844,115 A * | 7/1989 | Bowers ....................... 251/297 |
| 4,929,235 A | 5/1990 | Merry et al. |
| 5,211,370 A | 5/1993 | Powers |
| 6,145,810 A * | 11/2000 | Connolly et al. ........... 251/331 |
| 6,276,661 B1 | 8/2001 | Laird |

FOREIGN PATENT DOCUMENTS

| | | |
|---|---|---|
| DD | 0961045 | 3/1957 |
| DD | 1116001 | 7/1958 |
| EP | 0045668 | 2/1982 |
| EP | 0638290 | 2/1995 |

* cited by examiner

Primary Examiner—John Bastianelli
(74) Attorney, Agent, or Firm—Richard J. Godlewski

(57) ABSTRACT

An access valve (2) for a laparoscopic device or a intraluminal deployment device has a cylindrical diaphragm (8) with a longitudinal aperture (3), a flexible member (14) is passed circumferentially around the cylindrical diaphragm and an extension arrangement to pull the flexible member radially and/or tangentially to constrict the diaphragm to at least partially close off the longitudinal aperture. A rotary actuator may be used (12).

12 Claims, 3 Drawing Sheets

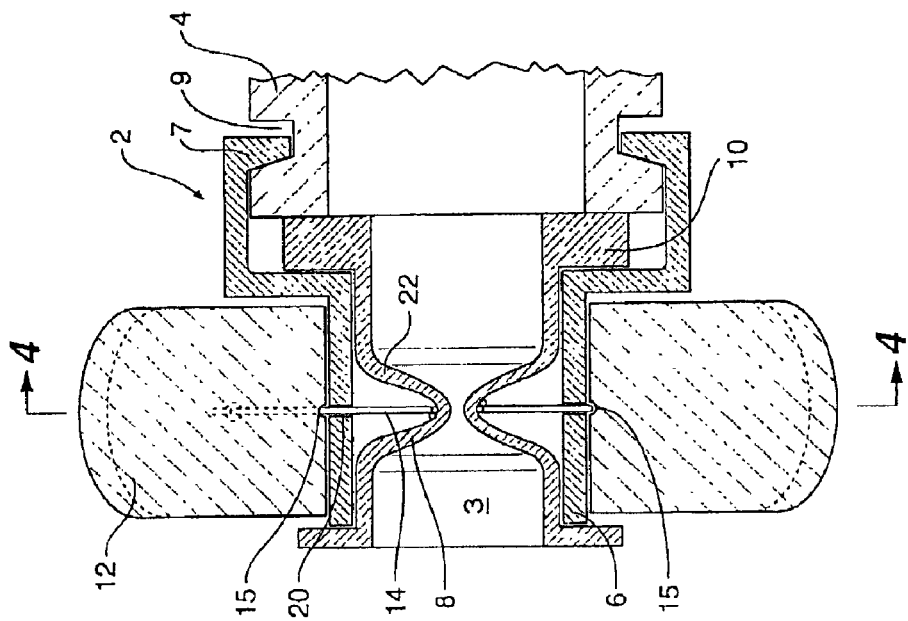
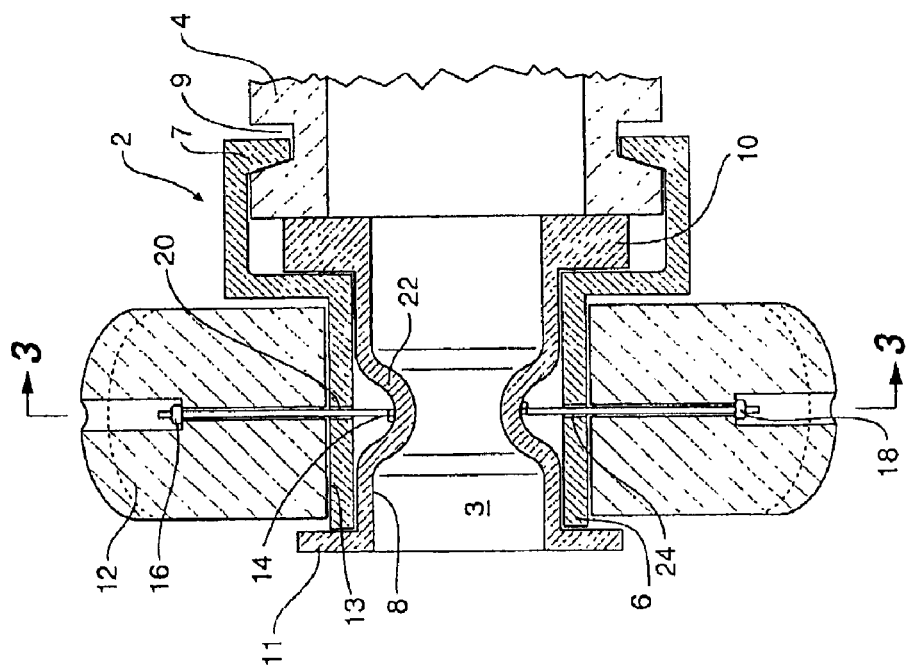

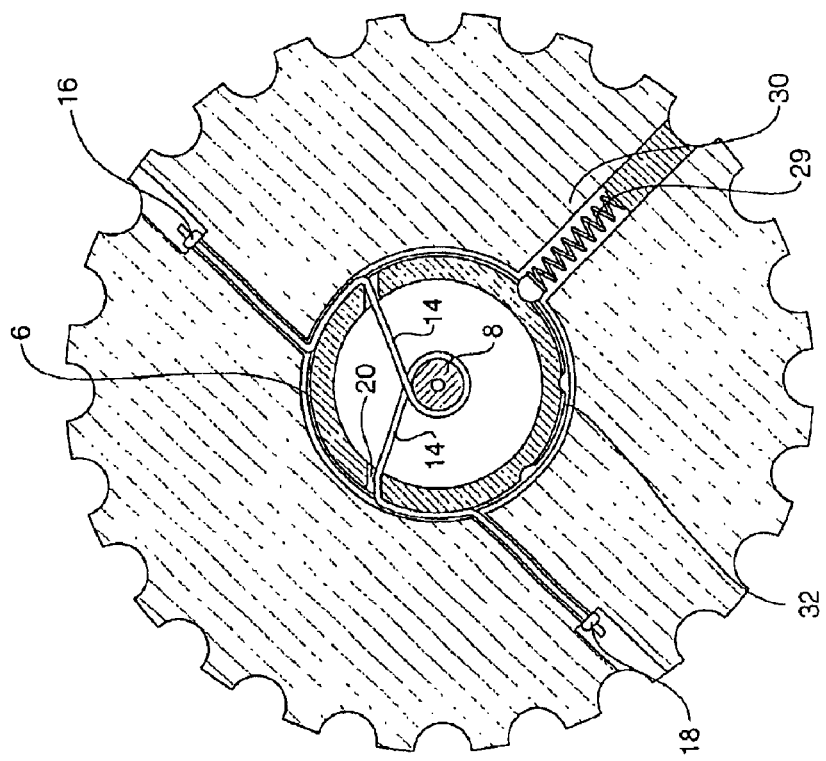
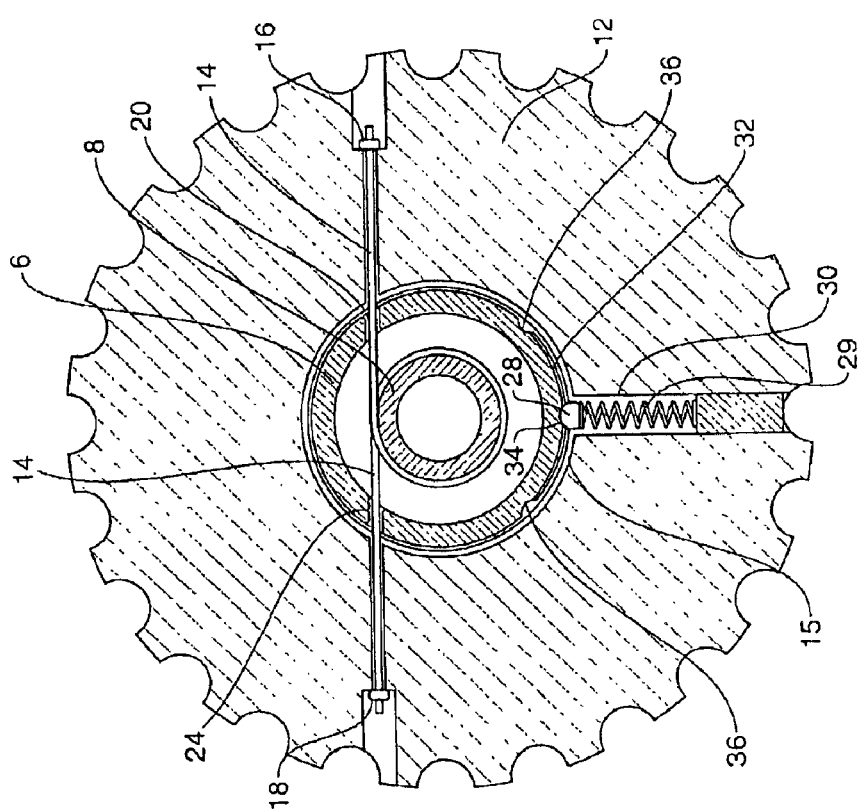

ACCESS VALVE

CROSS-REFERENCE TO RELATED APPLICATIONS

This application claims priority of Australian provisional application Serial No. PR 9290, filed Dec. 4, 2001.

TECHNICAL FIELD

This invention relates to a medical device, and in particular, to a fluid control or access valve and, more particularly, to an access valve of the constriction type.

BACKGROUND OF THE INVENTION

The invention will be discussed in particular in relation to fluid flow prevention and access valves in medical applications for instance where it is desired to seal around a catheter or other instrument in a manner which permits the catheter or other instrument to be passed through the access valve and the valve to form a seal against the walls of the catheter or other instrument to prevent loss of blood or other fluid.

SUMMARY OF THE INVENTION

It is an object of this invention to provide an access valve which can be controlled to vary the size of the aperture through the valve and be flexible so that a seal may be formed against an instrument or other object inserted through the access valve.

In one form therefore the invention is said to reside in an access valve having a cylindrical diaphragm with a longitudinal aperture therethrough, a flexible member passed circumferentially around the cylindrical diaphragm and extending substantially radially and/or tangentially therefrom and an extension arrangement to pull the flexible member radially and/or tangentially to constrict the diaphragm to at least partially close off the longitudinal aperture.

It will be seen that by this invention there is provided an arrangement by which an aperture through a cylindrical valve member can be closed off by constriction by the pulling of a flexible member on the outer surface of the cylindrical diaphragm. Depending on how much the flexible member is pulled radially and/or tangentially the cylindrical diaphragm can be completely constricted to prevent fluid flow through the valve or can be constricted to the extent that it closes around an instrument, for instance a catheter, passed through the valve.

In a preferred embodiment of the invention the cylindrical diaphragm may be supported in a substantially cylindrical housing into which the diaphragm is received. There may be apertures in the cylindrical housing through which the flexible members extend and some form of actuator to pull the flexible member mounted onto the cylindrical housing.

Preferably the cylindrical diaphragm is formed from a resilient material so that after constriction and release of the flexible member the valve reopens.

In one preferred embodiment the flexible member may be pulled from one of its ends and fastened to the cylindrical housing at its other end.

Alternatively the flexible member may be mounted at both of its ends to an actuator arrangement and hence the flexible member can be simultaneously pulled in substantially opposite directions to constrict the valve.

In the case of the access valve according to this invention used for medical tools the cylindrical housing may be mounted for instance onto an access point on a laparoscopic device. When it is required to insert a laparoscopic device through the valve the valve can be opened sufficiently to allow insertion of the device and then the access valve can be constricted around the device to prevent loss of blood or inflation gas from within a body cavity during operation of the device.

Alternatively the cylindrical housing may be mounted on a prosthesis delivery catheter and the access valve be adapted to close around a prosthesis delivery device.

In one embodiment the extension arrangement may be an actuator to pull the flexible member and the actuator may be mounted to the cylindrical housing.

In a preferred form of the invention the actuator to pull the flexible member may be a rotary actuator with respective ends of the flexible member joined to the rotary actuator whereby rotation of the rotary actuator with respect to the cylindrical housing causes the flexible member to be pulled to constrict the valve.

The rotary actuator may be retained in position by the flexible member extending from the rotary actuator and through the cylindrical housing. Alternatively the rotary actuator may be retained by a radial flange on the cylindrical housing or the cylindrical diaphragm. Alternatively the rotary actuator may be retained on the cylindrical housing by the ball and detent arrangement discussed in more detail below.

In a preferred form the cylindrical diaphragm of the valve may be constructed from a elastomeric material such as silicone rubber.

The flexible member may be a string, suture or band or other suitable material.

The rotary actuator may have a tactile indication of its action by means of a ball or other device acting into detents between the actuator and the cylindrical housing. The ball or other device acting into the detents may be spring loaded. The ball or other device may be mounted into the rotary actuator and travel in a circumferential groove in the cylindrical housing. This may also assist with retaining the rotary actuator on the cylindrical housing.

The rotary actuator may be adapted to be rotated through an angle of from 30 to 90 in one or both directions from a central rest position to cause the flexible member to be pulled which in turn causes the cylindrical diaphragm to be constricted.

In a preferred form of the invention there may be provided an additional apertured diaphragm seal in the valve to assist with closing off of the delivery catheter or other medical device.

In an alternative embodiment the invention may be said to reside in an access port on a laparoscopic catheter the access valve having a cylindrical diaphragm with a longitudinal aperture therethrough, a flexible member passed circumferentially around the cylindrical diaphragm and extending radially and/or tangentially therefrom and an extension arrangement to pull the flexible member radially and/or tangentially to constrict the diaphragm to at least partially close off the longitudinal aperture through the access port.

In a further form, the invention may be said to reside in an intraluminal deployment device having a catheter, the catheter having an access point at a proximal end thereof, the access point being adapted for the insertion of deployment devices or prostheses and a valve arrangement to close off the access point, the valve arrangement having a cylindrical diaphragm with a longitudinal aperture therethrough, a flexible member passed circumferentially around the cylindrical diaphragm and extending substantially radially and/or tangentially therefrom and an extension arrangement to pull the flexible member radially and/or tangentially to constrict the diaphragm to at least partially close off the longitudinal aperture in the valve arrangement.

BRIEF DESCRIPTION OF THE DRAWING

This then generally describes the invention, but to assist with understanding reference will now be made to the accompanying drawings which show preferred embodiments of the invention.
In the drawings:

FIG. 1 shows a cross-sectional view of one embodiment of a constriction valve according to this invention;

FIG. 2 shows the cross-sectional view shown in FIG. 1 with the valve in its partially constricted position;

FIG. 3 shows a cross-sectional view along the lines 3–3' in FIG. 1;

FIG. 4 shows a cross-sectional view along the lines 4–4' in FIG. 2;

DETAILED DESCRIPTION

Figure 5:
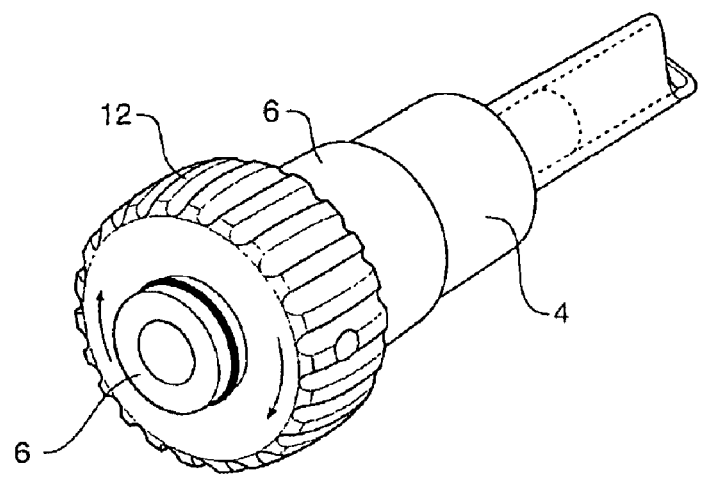
FIG. 5 shows a perspective view of a delivery catheter including a constriction valve according to this invention.

Now looking more closely at the drawings and particularly the embodiment shown in FIGS. 1 to 5 it will be seen that the access valve generally shown as 2 is mounted onto a catheter body 4. The access valve has a cylindrical housing 6 into which is received a cylindrical elastomeric diaphragm 8. The cylindrical elastomeric diaphragm 8 defines a cylindrical aperture 3 therethrough. The end of the cylindrical diaphragm 8 nearest the catheter 4 has an outwardly extending radial flange 10 which is clamped against the end of the catheter by means of the cylindrical housing 6. The flange 7 on the cylindrical housing 6 is received in slot 9 in the catheter body 4 to hold and seal the valve 2 to the catheter body 4. A rotary actuator 12 is mounted onto the cylindrical housing 6 and retained in position by a radial flange 11 extending from the external end of the cylindrical diaphragm. A string 14 is mounted into the rotary actuator with a knot 16 at one end and then passes through an aperture 20 in the cylindrical housing 6 and then is wound preferably twice around the cylindrical diaphragm 8 preferably in a recessed region 22 and then passes through a further aperture 24 in the cylindrical housing before being fixed by knot 18 again in the rotary actuator. Rotation of the rotary actuator 12 with respect to the cylindrical housing 6 will cause the string 14 to be pulled in both directions at once and hence the cylindrical diaphragm 8 to be constricted.

The internal cylindrical surface 13 of the rotary actuator 12 has a circumferential groove 15 which allows the string 14 to extend around the outside of the cylindrical housing 6 when the rotary actuator 12 is rotated. Alternatively the cylindrical housing 6 may have a circumferential groove on its outer surface to allow the string 14 to extend around the outside of the cylindrical housing 6 when the rotary actuator 12 is rotated.

As particularly shown in FIGS. 3 and 4 a detent arrangement having a ball 28 loaded by a spring 29 in an aperture 30 in the rotary actuator runs in a groove 32 in the cylindrical housing 6. The groove 32 has a central recess 34 and end recesses 36. There may also be further recesses or detents between the central recess and the end recesses. The rotary actuator may be rotated in either direction to cause constriction of the constriction valve, and the detents provide tactile feel the action of the valve.

Particularly as shown in FIG. 4 when the rotary actuator is moved through perhaps 45° of rotation, it will be seen that the flexible member 14 has been pulled tangentially in both directions and the cylindrical diaphragm has been stretched radially inwards or constricted and the valve partially closed off. Rotation of the rotary actuator back to the central position where the detent ball 28 is received in depression 34 will cause the sutures to loosen again so that the resilient cylindrical diaphragm will retain its original shape as shown in FIGS. 1 and 3. Depending upon the number of turns of the flexible member around the cylindrical diaphragm rotation of the rotary actuator may be up to 90 or more in either direction to enable complete closing off of the valve.

Figure 6:
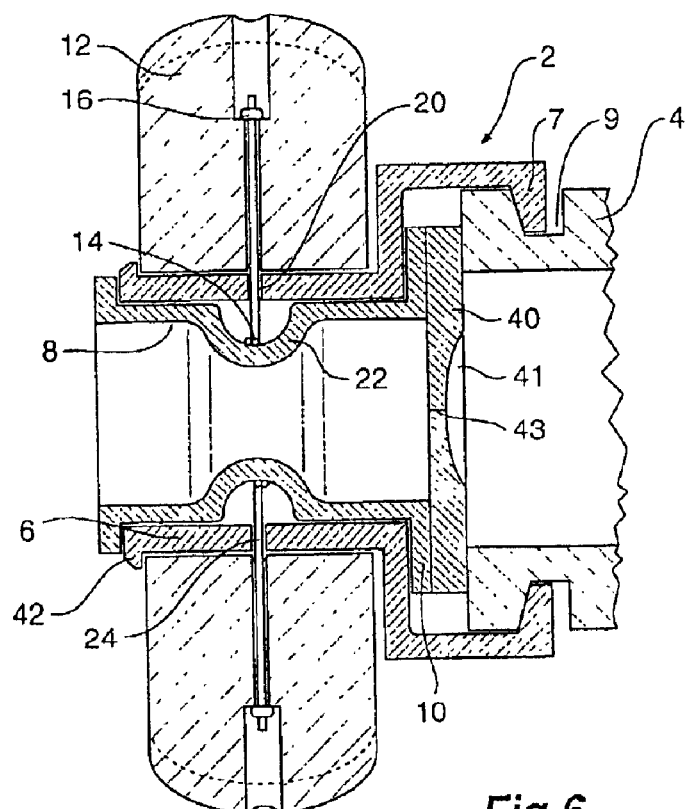
FIG. 6 shows an alternative embodiment of constriction valve including a split diaphragm according to the invention.

In the embodiment of constriction valve shown in FIG. 6 the sealing action of the valve as discussed above is assisted by means of an apertured diaphragm 40 which is also clamped between the cylindrical housing 6 and the catheter body 4. The apertured diaphragm 40 has an aperture or a slit 41 completely through it or a half slit 41, 43 from each side crossed at right angles to provide extra sealing for the time that the valve is opened to allow an instrument to be passed through it. The apertured diaphragm may be formed from a silicone rubber and may be formed integrally with or separately from the cylindrical diaphragm.

In this embodiment the rotary actuator is be retained by a radially outwardly extending flange 42. This flange may alternatively be positioned so that it engages in a groove on the internal cylindrical surface of the rotary actuator. The rotary actuator may be pushed on over the flange to click into position to retain it.

It will be seen that by this invention there is provided an access or constriction valve arrangement which will close over a range of diameters of devices passed through the valve or can close completely down to be self sealing.

Throughout this specification various indications have been given as to the scope of the invention but the invention is not limited to any one of these but may reside in two or more combined together. The examples are given for illustration only and not for limitation.

What is claimed is:

1. An access valve comprising a substantially cylindrical housing, a longitudinal aperture through the cylindrical housing, a cylindrical diaphragm in the longitudinal aperture, the cylindrical diaphragm being formed from a resilient material, a flexible member passed circumferentially around the cylindrical diaphragm at least for one full turn, apertures in the cylindrical housing through which the flexible member extends and a rotary actuator on the cylindrical housing with respective ends of the flexible member joined to the rotary actuator, whereby rotation of the rotary actuator with respect to the cylindrical housing causes the flexible member to be pulled through the apertures to constrict the cylindrical diaphragm to at least partially close off the longitudinal aperture.

2. An access valve as in claim 1 wherein the rotary actuator is retained in position on the cylindrical housing by the flexible member extending from the rotary actuator to the cylindrical diaphragm through the apertures in the cylindrical housing.

3. An access valve as in claim 1 wherein the rotary actuator is retained in position on the cylindrical housing by a radial flange on the cylindrical housing or on the cylindrical diaphragm.

4. An access valve as in claim 1 wherein the cylindrical diaphragm is constructed from a silicone rubber.

5. An access valve as in claim 1 wherein the flexible member is a string, suture or band or other suitable material.

6. An access valve as in claim 1 further including a ball and detent arrangement between the rotary actuator and the cylindrical housing whereby tactile feel of the action of the rotary actuator is provided.

7. An access valve as in claim 1 mounted onto an access location of a laparoscopic device.

8. An access valve as in claim 1 mounted onto a prosthesis delivery device.

9. An access valve as in claim 1 further including an additional apertured diaphragm seal in the valve to assist with a sealing action.

10. An access valve as in claim 1 further including a recessed region on an outer surface of the cylindrical diaphragm to act as a guide for the flexible member.

11. A laparoscopic device having an access port with a longitudinal aperture therethrough, the access port comprising a substantially cylindrical housing, a longitudinal aperture through the cylindrical housing, a cylindrical diaphragm in the longitudinal aperture, the cylindrical diaphragm being formed from a resilient material, a flexible member passed circumferentially around the cylindrical diaphragm at least for one full turn, apertures in the cylindrical housing through which the flexible member extends and a rotary actuator on the cylindrical housing with respective ends of the flexible member joined to the rotary actuator, whereby rotation of the rotary actuator with respect to the cylindrical housing causes the flexible member to be pulled through the apertures to constrict the diaphragm to at least partially close off the longitudinal aperture through the access port.

12. An intraluminal deployment device having a catheter, the catheter having an access point at a proximal end thereof, the access point being adapted for the insertion of a deployment device or a prosthesis and an access valve to close off the access point, the access valve comprising a substantially cylindrical housing, a longitudinal aperture through the cylindrical housing, a cylindrical diaphragm in the longitudinal aperture, the cylindrical diaphragm being formed from a resilient material, a flexible member passed circumferentially around the cylindrical diaphragm at least for one full turn, apertures in the cylindrical housing through which the flexible member extends and a rotary actuator on the cylindrical housing with respective ends of the flexible member joined to the rotary actuator, whereby rotation of the rotary actuator with respect to the cylindrical housing causes the flexible member to be pulled through the apertures to constrict the diaphragm to at least partially close off the longitudinal aperture in the access valve.

* * * * *